United States Patent
Iwamoto et al.

(10) Patent No.: US 10,591,470 B2
(45) Date of Patent: Mar. 17, 2020

(54) IMMUNOCHROMATOGRAPHIC ANALYSIS METHOD

(71) Applicant: TANAKA KIKINZOKU KOGYO K.K., Chiyoda-ku, Tokyo (JP)

(72) Inventors: Hisahiko Iwamoto, Hiratsuka (JP); Kazuyoshi Mochiduki, Hiratsuka (JP); Daisuke Ito, Hiratsuka (JP); Yuya Kato, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 534 days.

(21) Appl. No.: 15/301,651

(22) PCT Filed: Mar. 31, 2015

(86) PCT No.: PCT/JP2015/060284
§ 371 (c)(1),
(2) Date: Oct. 3, 2016

(87) PCT Pub. No.: WO2015/152312
PCT Pub. Date: Oct. 8, 2015

(65) Prior Publication Data
US 2017/0023559 A1   Jan. 26, 2017

(30) Foreign Application Priority Data
Apr. 4, 2014   (JP) ................. 2014-077861

(51) Int. Cl.
| G01N 31/00 | (2006.01) |
| G01N 33/53 | (2006.01) |
| G01N 33/543 | (2006.01) |
| B01D 15/10 | (2006.01) |
| B01D 15/38 | (2006.01) |

(52) U.S. Cl.
CPC ....... *G01N 33/54306* (2013.01); *B01D 15/10* (2013.01); *B01D 15/3809* (2013.01); *B01D 15/3857* (2013.01); *G01N 33/543* (2013.01); *G01N 33/54386* (2013.01)

(58) Field of Classification Search
None
See application file for complete search history.

(56) References Cited

U.S. PATENT DOCUMENTS

| 4,999,287 A * | 3/1991 | Allen ................. C12Q 1/26 422/408 |
| 2009/0047673 A1 * | 2/2009 | Cary .................. C12Q 1/6834 435/6.11 |
| 2009/0275060 A1 * | 11/2009 | Place ................. G01N 33/74 435/7.92 |
| 2011/0070658 A1 * | 3/2011 | Rutter ................ G01N 33/558 436/501 |
| 2012/0288962 A1 | 11/2012 | Sakakibara et al. |

FOREIGN PATENT DOCUMENTS

| EP | 1494030 A2 | 1/2005 |
| EP | 2306194 A1 | 4/2011 |
| EP | 2535713 A1 | 12/2012 |
| JP | 2001-013141 A | 1/2001 |
| JP | 2004-154074 A | 6/2004 |
| JP | 2009-052945 A | 3/2009 |
| JP | 2009-063482 A | 3/2009 |
| JP | 2009-085700 A | 4/2009 |
| JP | 2011-209140 A | 10/2011 |
| JP | 2012-159440 A | 8/2012 |
| JP | 2012-189346 A | 10/2012 |
| JP | 2012-251789 A | 12/2012 |
| JP | 2013-049645 A | 3/2013 |
| JP | 2013-195403 A | 9/2013 |
| WO | WO 2010/116979 A1 | 10/2010 |
| WO | WO 2013/141122 A1 | 9/2013 |

OTHER PUBLICATIONS

PCT, International Search Report Report for PCT/JP2015/060284, dated Jun. 23, 2015.
PCT, International Preliminary Report on Patentability for PCT/JP2015/060284, dated Apr. 11, 2016.
JP, Office Action for Japanese Appl. No. 2014-077861, dated Apr. 7, 2015.
EP, Extended European Search Report concerning application No. 15772558.1, dated Apr. 10, 2017
CN, Office Action for Application No. 201580018517.6, dated Jun. 1, 2017.

* cited by examiner

*Primary Examiner* — Lisa V Cook
(74) *Attorney, Agent, or Firm* — Orrick, Herrington & Sutcliffe LLP; Joseph A. Calvaruso; K. Patrick Herman

(57) ABSTRACT

An object is to provide an immunochromatographic analysis method capable of shortening the developing time without decreasing the detection sensitivity, and also capable of reducing the return of the liquid of a developed component, and a method for detecting a detection target contained in an analyte using an immunochromatographic analysis device including an absorption part composed of glass fiber, wherein the analyte and a labeling substance are developed in a chromatography medium part as a mobile phase in the presence of a nonionic surfactant, and the detection target is detected in a detection part is provided.

18 Claims, 1 Drawing Sheet

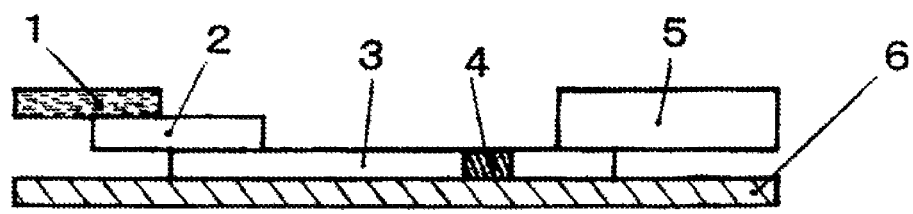

IMMUNOCHROMATOGRAPHIC ANALYSIS METHOD

TECHNICAL FIELD

This application claims priority to Application Nos. PCT/JP2015/060284 and JP 2014-077861. The present invention relates to an immunochromatographic analysis method, an immunochromatographic analysis device, and an immunochromatographic analysis kit.

BACKGROUND ART

Recently, the importance of an immunoassay by immunochromatography which does not require the pretreatment of an analyte as a simple in vitro diagnostic kit or a portable diagnostic device for detecting an antigen in a sample solution utilizing a specific reactivity of an antibody has been increasing. In particular, a test kit for a pathogen such as a virus or a bacterium is an immunochromatography device which is familiar and widely used also in an ordinary hospital and clinic.

The simplest structure of the immunochromatography device is a structure in which a sample addition part, a labeling substance retaining part, a chromatography medium having a detection part supported thereon, and an absorption part are mutually connected to each other.

Among these, for the absorption part, cotton, a nonwoven material, a filter paper, or the like composed of cellulose fiber, pulp fiber, or the like has been conventionally used. However, an absorption material composed only of such a material has a poor ability to retain a developed component which has been once absorbed, and as a result, there is a problem that the backward flow of the developed component from the absorption material occurs.

Conventionally, in order to prevent such backward flow of the developed component from the absorption material, an attempt that the absorption material is formed using high water-absorbing fiber has been made (PTL 1). Further, an absorption material containing a water-absorbing polymer has been proposed (PTL 2).

CITED REFERENCES

Patent Documents

Patent Document 1: JP-A-2009-63482
Patent Document 2: JP-A-2012-189346

DISCLOSURE OF THE INVENTION

Problems to be Solved by the Invention

However, the absorption material containing high water-absorbing fiber disclosed in PTL 1 has a problem that the absorption speed for a developed component is low, and the developed component is not sufficiently absorbed in the absorption material within a specified reaction time (10 to 15 minutes), and due to an excess liquid sample remaining on a chromatography medium, a positive signal appearing in a detection part is blurred, or a colored labeling substance is not sufficiently recovered, and therefore, a background signal is increased.

Further, the absorption material containing a water-absorbing polymer disclosed in PTL 2 solves the above problem but has a problem that the absorbing polymer is likely to fall down during production.

Further, when the developing speed is increased for shortening the developing time of a developed component, since the absorption efficiency for the developed component in the absorption part is low, the developed component cannot be completely absorbed in the absorption part, and the return of the liquid of the developed component occurs, and therefore, a false-positive result occurs.

Therefore, an object of the present invention is to provide an immunochromatographic analysis method capable of shortening the developing time without decreasing the detection sensitivity, and also capable of reducing the return of the liquid of a developed component.

Means for Solving the Problems

The present invention is as follows.
1. An immunochromatographic analysis method, which is a method for detecting a detection target contained in an analyte using an immunochromatographic analysis device which includes a sample addition part, a labeling substance retaining part, a chromatography medium part having a detection part supported thereon, and an absorption part composed of glass fiber, comprising the following steps (1) to (4):
(1) a step of adding an analyte-containing solution obtained by diluting the analyte with an analyte dilution solution to the sample addition part;
(2) a step of recognizing the detection target by a labeling substance retained in the labeling substance retaining part;
(3) a step of developing the analyte and the labeling substance in the chromatography medium part as a mobile phase in the presence of a nonionic surfactant; and
(4) a step of detecting the detection target in the developed mobile phase in the detection part.
2. The method as described in 1 above, wherein the nonionic surfactant is contained in at least one of the sample addition part and the analyte dilution solution.
3. The method as described in 2 above, wherein the content of the nonionic surfactant in the sample addition part is from 0.05 to 5 mg per $cm^2$.
4. The method as described in 2 above, wherein the content of the nonionic surfactant in the analyte dilution solution is from 0.05 to 10 mass %.
5. The method as described in any one of 1 to 4 above, wherein the HLB value of the nonionic surfactant is 10 or more.
6. The method as described in any one of 1 to 5 above, wherein the chromatography medium part contains an anionic surfactant.
7. The method as described in 6 above, wherein the content of the anionic surfactant in the chromatography medium part is from 0.02 to 4 mass %.
8. The method as described in any one of 1 to 7 above, wherein the chromatography medium part is composed of nitrocellulose.
9. The method as described in any one of 1 to 8 above, wherein the filtering time of the absorption part is from 20 seconds to 110 seconds, and the density thereof is from 150 to 500 $mg/cm^3$.
10. An immunochromatographic analysis device, sequentially comprising a sample addition part, a labeling substance retaining part, a chromatography medium part having a detection part supported thereon, and an absorption part, wherein the sample addition part retains a nonionic surfactant in a dry state, and the absorption part is composed of glass fiber.

11. An immunochromatographic analysis kit, comprising an immunochromatography device, which sequentially includes a sample addition part, a labeling substance retaining part, a chromatography medium part having a detection part supported thereon and an absorption part, and an analyte dilution solution for diluting a detection target contained in an analyte, wherein the absorption part is composed of glass fiber, and the analyte dilution solution contains a nonionic surfactant.

Effect of the Invention

The immunochromatographic analysis method of the present invention is capable of shortening the developing time without decreasing the detection sensitivity by using an immunochromatographic analysis device in which an analyte and a labeling substance are developed in a chromatography medium part as a mobile phase in the presence of a nonionic surfactant.

In a conventional immunochromatographic analysis method, when the developing time is shortened, the developed component cannot be completely absorbed in the absorption part, and the return of the liquid of the developed component occurs, however, in the immunochromatographic analysis method of the present invention, glass fiber is used for the absorption part, and therefore, the return of the liquid of the developed component is reduced, and thus, the occurrence of a false-positive result can be avoided.

BRIEF DESCRIPTION OF DRAWINGS

FIG. 1 shows a structure of an immunochromatographic analysis device.

EMBODIMENTS FOR CARRYING OUT THE INVENTION

Hereinafter, embodiments for carrying out the present invention will be described.

The immunochromatographic analysis method of the present invention is a method for detecting a detection target contained in an analyte in the presence of a nonionic surfactant using an immunochromatographic analysis device which includes a sample addition part, a labeling substance retaining part, a chromatography medium part having a detection part supported thereon, and an absorption part composed of glass fiber.

Hereinafter, the immunochromatographic analysis device which can be used in the present invention and a method for using the device will be described.

As shown in FIG. 1, the immunochromatographic analysis device sequentially includes a sample addition part (also referred to as "sample pad") (1), a labeling substance retaining part (also referred to as "conjugate pad") (2), a chromatography medium part (3), a detection part (4), and an absorption part (5), and also includes a backing sheet (6). The term "sequentially" refers to the order of the respective parts in which a sample is developed in the immunochromatographic analysis device of the present invention. The structures, specifications, and embodiments of the respective parts are as follows.

The sample addition part (1) is a part where a sample is dropped in the immunochromatographic analysis device, and is made of any material as long as the material is usually used for immunochromatography. In general, for the sample addition part, a membrane of glass fiber or cellulose which absorbs and retains a sample is used.

It is preferred that a nonionic surfactant is contained in the sample addition part in advance. By doing this, the decrease in the detection sensitivity due to adsorption of an analyte on the addition member of the sample part is prevented. In addition, by decreasing the surface tension of a sample, the developing time is shortened.

The content of the nonionic surfactant in the sample addition part is preferably from 0.05 to 5 mg, more preferably from 0.2 to 5 mg, further more preferably from 0.2 to 2.5 mg.

This is because when the content of the nonionic surfactant in the sample addition part is 0.05 mg or more, the surface tension of a sample can be significantly decreased, and when the content thereof is 5 mg or less, the effect of denaturation on a sample of the nonionic surfactant can be suppressed.

Examples of the nonionic surfactant include polyoxyethylene alkyl ethers, polyoxyethylene/polyoxypropylene alkyl ethers, polyoxyethylene sorbitan fatty acid esters (trade name "TWEEN" series), polyoxyethylene p-t-octylphenyl ethers (trade name: "TRITON" series), polyoxyethylene p-t-nonylphenyl ethers (trade name: "TRITON N" series), alkyl polyglucosides, fatty acid diethanolamide, alkyl monoglyceryl ethers, NP-40 (manufactured by Sigma-Aldrich Corporation), and IGAPEL CA-520 (manufactured by Sigma-Aldrich Corporation).

The HLB value of the nonionic surfactant is preferably 10 or more, more preferably 11.0 or more, further more preferably 12.4 or more. The upper limit thereof is not particularly limited, but is preferably 18 or less.

When the HLB value of the nonionic surfactant is 10 or more, the effect of denaturation on a sample of hydrophobic interaction can be suppressed. When the HLB value of the nonionic surfactant is 18 or less, the effect of denaturation on a sample of hydrophobic interaction can be suppressed.

The CMC value of the nonionic surfactant is preferably from 5 μmol to 60 mmol, more preferably from 10 μmol to 60 mmol, further more preferably from 12 μmol to 60 mmol.

When the CMC value of the nonionic surfactant is 5 μmol or more, the effect of addition thereof can be exhibited. Further, when the CMC value thereof is 60 mmol or less, the amount of use can be decreased, and therefore, it is economical.

The nonionic surfactant when it is contained in the sample addition part is prepared as an aqueous solution at a concentration of 0.05 to 10 mass %, and a member to be used for the sample addition part is immersed in this solution, followed by vacuum drying or natural drying, whereby the sample addition part containing the nonionic surfactant is prepared.

The labeling substance retaining part (2) contains a labeling substance (marker substance), which will be described later, bound to an antibody which binds to a detection target in advance. The detection target is bound to the antibody when the detection target migrates in the labeling substance retaining part and labeled. The labeling substance retaining part is composed of, for example, a glass fiber non-woven fabric, a cellulose membrane, or the like.

The chromatography medium part (3) is a developing part in a chromatograph. The chromatography medium part is an inactive membrane composed of a microporous material showing a capillary phenomenon. Examples of a membrane which does not have reactivity with a detection reagent to be used in chromatography, an immobilization reagent, a detection target, or the like include a membrane made of nitrocellulose (hereinafter also referred to as "nitrocellulose membrane").

The membrane made of nitrocellulose may be any as long it contains nitrocellulose as a main component, and a membrane which contains nitrocellulose as a main material such as a pure product or a nitrocellulose mixed product may be used, however, there is no problem when other materials are used. Examples of such other materials include cellulose membranes, nylon membranes, and porous plastic fabrics (polyethylene and polypropylene).

It is also possible to further contain a substance which promotes the capillary phenomenon in the nitrocellulose membrane. As the substance, a substance which decreases the surface tension of the membrane surface and brings hydrophilicity is preferred. For example, a substance which has amphiphilic activity such as a saccharide, an amino acid derivative, a fatty acid ester, any of a variety of synthetic surfactants, or an alcohol, and does not have an effect on the migration of a detection target on an immunochromatograph, and does not affect the development of the color of a marker substance (for example, colloidal gold or the like) is preferred.

Examples of the substance include anionic surfactants, amphoteric surfactants, nonionic surfactants, and glycerin, and among these, anionic surfactants are preferred. Examples of the anionic surfactants include sodium dodecylbenzene sulfonate (SDBS), sodium dodecyl sulfonate (SDS), sodium C12-18 alkyl sulfonate (sodium alkane sulfonate), sodium dialkyl sulfosuccinate, and sodium cholate.

The substance is particularly preferably sodium dodecyl sulfonate (SDS) or sodium C12-18 alkyl sulfonate (sodium alkane sulfonate).

The content of the anionic surfactant in the chromatography medium part is preferably from 0.02 to 4 mass %, more preferably from 0.02 to 1 mass %, further more preferably from 0.1 to 1 mass %.

When the content of the anionic surfactant in the chromatography medium part is 0.02 mass % or more, sufficient sensitivity and an effect of shortening the detection time can be obtained, and the decrease in the storage stability can be avoided. When the content of the anionic surfactant in the chromatography medium part is 4 mass % or less, the occurrence of a non-specific reaction in a negative analyte can be prevented.

The anionic surfactant to be contained in the chromatography medium part is prepared as an aqueous solution at a concentration of 0.1 to 10 mass %, and a nitrocellulose membrane is immersed in this solution, followed by vacuum drying or natural drying, whereby the chromatography medium containing the anionic surfactant is prepared. Other than the above method, a method in which an additive is directly added to a formed membrane, followed by drying or the like may be adopted, and the method is not limited to these methods as long as the anionic surfactant can be contained in a formed membrane by external addition.

The thus prepared nitrocellulose membrane is porous and shows a capillary phenomenon. The index of this capillary phenomenon can be confirmed by measuring a water absorption speed (water absorption time: capillary flow time). The water absorption speed has an effect on the detection sensitivity and the test time.

The form and size of the nitrocellulose membrane as the chromatography medium to be used in the immunochromatographic analysis method of the present invention are not particularly limited and may be any as long as they are appropriate for the actual operation and the observation of the reaction result.

In addition, in order to further simplify the operation, it is preferred that a support composed of a plastic or the like is provided on the rear surface of the chromatography medium having a reaction region formed on the surface thereof. The properties of this support are not particularly limited, however, in the case where the observation of the measurement result is performed by visual determination, the support preferably has a color which is not similar to the color caused by the labeling substance, and is generally preferably colorless or white.

The detection part (4) is formed on the chromatography medium part (3), that is, a reaction region in which a substance which specifically binds to a detection target, for example, an antibody is immobilized at an arbitrary position as an immobilizing reagent is formed.

As a method for immobilizing the immobilizing reagent on the chromatography medium, there are a method in which the immobilizing reagent is directly immobilized on the chromatography medium through a physical or chemical means and an indirect immobilization method in which the immobilizing reagent is physically or chemically bound to fine particles such as latex particles, and the fine particles are trapped in the chromatography medium.

In the direct immobilization method, physical adsorption may be utilized, or a covalent bond may be used. In the case of a nitrocellulose membrane, physical adsorption can be performed. In the case of using a covalent bond, in order to activate the chromatography medium, cyanogen bromide, glutaraldehyde, carbodiimide, or the like is generally used, however, any method can be used.

As the indirect immobilization method, there is a method in which the immobilizing reagent is bound to insoluble fine particles, and thereafter immobilized on the chromatography medium. As the particle diameter of the insoluble fine particles, a size can be selected so that the fine particles are trapped in the chromatography medium but cannot migrate therein, and the fine particles preferably have an average particle diameter of about 5 μm or less.

As the particles, various particles to be used for an antigen-antibody reaction are known, and also in the present invention, these known particles can be used. Examples thereof include fine particles of an organic polymeric substance such as latex particles of an organic polymer obtained by emulsion polymerization method such as polystyrene, a styrene-butadiene copolymer, a styrene-methacrylate copolymer, polyglycidyl methacrylate, or an acrolein-ethylene glycol dimethacrylate copolymer, fine particles of gelatin, bentonite, agarose, cross-linked dextran, or the like, and inorganic particles of an inorganic oxide such as silica, silica-alumina, or alumina or inorganic particles in which a functional group is introduced into an inorganic oxide by a silane-coupling treatment or the like.

In the present invention, from the viewpoint of ease of adjustment of sensitivity or the like, direct immobilization is preferred. Further, in order to immobilize the immobilizing reagent on the chromatography medium, various methods can be used. For example, various techniques such as a microsyringe, a pen with an adjustment pump, and ink injection printing can be used. The form of the reaction region is not particularly limited, however, immobilization can also be performed in the form of a circular spot, a line extending in a direction perpendicular to the development direction in the chromatography medium, a numeric character, a letter, a symbol such as + or −, or the like.

After the immobilizing reagent is immobilized, in order to prevent the decrease in the analysis accuracy due to non-specific adsorption, according to need, a blocking treatment can be performed for the chromatography medium by a known method.

In general, in the blocking treatment, a protein such as bovine serum albumin, skim milk, casein, or gelatin is preferably used. After such a blocking treatment, according to need, for example, washing may be performed by using one surfactant or two or more surfactants such as TWEEN 20, TRITON X-100, and SDS in combination.

The absorption part (5) is provided for absorbing the developing solution at an end of the chromatography medium. In the immunochromatographic analysis device of the present invention, the absorption part is composed of glass fiber. When the absorption part is composed of glass fiber, the return of the liquid of the developed component can be greatly reduced.

By performing immunochromatographic analysis in the presence of a nonionic surfactant, the developing time is shortened, however, if the absorption efficiency of the developed component in the absorption part is low, the developed component cannot be completely absorbed in the absorption part, and the return of the liquid of the developed component occurs.

Here, when a member which is widely used such as cellulose fiber is used as an absorbent in the absorption part, the absorption speed is low, and also the diffusion speed of the developed component, the nonionic surfactant, or the like in the absorption part is also low, and therefore, the effect of suppression of adsorption of the nonionic surfactant becomes obvious, and thus, the backward flow of the developed component occurs.

However, the absorption part composed of glass fiber has a high water absorption speed, and the developed component promptly diffuses in the absorption part, so that the developed component, the nonionic surfactant, or the like becomes thin, and therefore, the backward flow is suppressed. That is, by using glass fiber for the absorption part, the return of the liquid of the developed component can be greatly reduced, and thus, the developing time can be shortened, and also a false-positive result can be reduced.

In the above-mentioned sample addition part, the density of the nonionic surfactant per volume is high, and therefore, an effect of suppressing the adsorption on the member is exhibited, however, in the absorption part, the volume is larger than that of the addition part, and therefore, the density of the nonionic surfactant per volume of the absorption part is low, and therefore, the suppression of adsorption is alleviated, and thus, the backward flow of the developed component from the absorption member is less likely to occur.

The filtering time of the absorption part is preferably from 20 seconds to 110 seconds, more preferably from 20 to 105 seconds, further more preferably from 20 to 100 seconds.

When the filtering time of the absorption part is 20 seconds or more, a minimum time required for the reaction can be ensured, and the detection sensitivity is never decreased. When the filtering time of the absorption part is 110 seconds or less, the determination time can be shortened. The filtering time of the absorption part can be measured in accordance with JIS P 3801:1995.

Further, the density of the absorption part to be used is preferably from 150 to 500 mg/cm$^3$, more preferably from 200 to 500 mg/cm$^3$, further more preferably from 200 to 350 mg/cm$^3$. By using glass fiber having a density of 200 to 350 mg/cm$^3$, the return of the liquid of the developed component can be greatly reduced.

The backing sheet (6) is a base material. By applying an adhesive to one surface or bonding an adhesive tape to one surface, the surface has adhesiveness, and on the adhesive surface, part or all of the sample addition part (1), the labeling substance retaining part (2), the chromatography medium part (3), the detection part (4), and the absorption part (5) are provided in close contact with the surface. The backing sheet (6) is not particularly limited as the base material as long as it is impermeable to a sample solution and also is impermeable to moisture by applying the adhesive.

The immunochromatographic analysis method of the present invention includes the following steps (1) to (4), and detects a detection target contained in an analyte using the above-mentioned immunochromatographic analysis device:

(1) a step of adding an analyte-containing solution obtained by diluting the analyte with an analyte dilution solution to the sample addition part;

(2) a step of recognizing the detection target by a labeling substance retained in the labeling substance retaining part;

(3) a step of developing the analyte and the labeling substance in the chromatography medium part as a mobile phase in the presence of a nonionic surfactant; and (4) a step of detecting the detection target in the developed mobile phase in the detection part.

Hereinafter, the respective steps will be described.

(1) Step of Adding Analyte-Containing Solution Obtained by Diluting Analyte with Analyte Dilution Solution to Sample Addition Part In the step (1), in the first place, an analyte-containing solution is prepared by adjusting or diluting an analyte with an analyte dilution solution to such a concentration that the analyte migrates smoothly in the immunochromatography medium without decreasing the measurement accuracy. In the second place, the analyte-containing solution is dropped on the sample addition part (1) in a predetermined amount (generally from 0.1 to 2 mL). When the analyte-containing solution is dropped, the analyte-containing solution starts to migrate in the sample addition part (1).

The analyte dilution solution preferably contains a nonionic surfactant. According to this, the developing time is shortened without decreasing the detection sensitivity. As the nonionic surfactant, the same nonionic surfactant as described above can be used. The content of the nonionic surfactant in the analyte dilution solution is preferably from 0.05 to 10 mass %, more preferably from 0.05 to 5 mass %, further more preferably from 0.05 to 3.5 mass %.

When the content of the nonionic surfactant in the analyte dilution solution is 0.05 mass % or more, the decrease in the detection sensitivity due to adsorption of the analyte on the member of the sample dropping part is prevented, and also, by decreasing the surface tension of the analyte dilution solution, the developing time can be shortened.

It is because when the content of the nonionic surfactant in the analyte dilution solution is 10 mass % or less, the effect of denaturation on a sample of the nonionic surfactant can be suppressed.

Examples of the analyte containing a detection target include biological samples, that is, whole blood, serum, plasma, urine, saliva, sputum, a nasal swab, a pharyngeal swab, spinal fluid, amniotic fluid, nipple discharge fluid, tear, sweat, exudates from the skin, and extracts from tissues, cells, and feces, and in addition thereto, milk, eggs, wheat, beans, beef, pork, chicken, and extracts from foods and the like containing the same.

(2) Step of Recognizing Detection Target by Labeling Substance Retained in Labeling Substance Retaining Part The step (2) is a step in which the analyte-containing solution added to the sample addition part in the step (1) is migrated to the labeling substance retaining part (2), and the detection target in the analyte is recognized by the labeling substance retained in the labeling substance retaining part.

The labeling substance labels a substance which specifically binds to the detection target, for example, an antibody. In the labeling of a detection reagent in the immunochromatography method, in general, an enzyme or the like is also used, however, it is preferred to use an insoluble carrier as the labeling substance because it is suitable for visually determining the presence of the detection target. The labeled detection reagent can be prepared by sensitizing the detection reagent to the insoluble carrier.

As the insoluble carrier to serve as the labeling substance, colloidal metal particles such as gold, silver, or platinum, colloidal metal oxide particles such as iron oxide, colloidal non-metal particles such as sulfur, latex particles composed of a synthetic polymer, or other material can be used. In particular, colloidal gold is preferred because detection is simple and easy.

The insoluble carrier is the labeling substance suitable for visually determining the presence of the detection target, and is preferably a colored substance in order to facilitate the visual determination. The colloidal metal particles and the colloidal metal oxide particles exhibit a specific natural color per se according to the particle diameter, and the color can be utilized as a label.

Examples of the colloidal metal particles and the colloidal metal oxide particles which can be used as the labeling substance include colloidal gold particles, colloidal silver particles, colloidal platinum particles, colloidal iron oxide particles, and colloidal aluminum hydroxide particles.

In particular, colloidal gold particles and colloidal silver particles are preferred because when the particles have an appropriate particle diameter, the colloidal gold particles exhibit a red color, and the colloidal silver particles exhibit a yellow color.

In the case where as the colloidal metal particles, for example, colloidal gold particles are used, a commercially available product may be used. Alternatively, colloidal gold particles can be prepared by a conventional method, for example, a method in which chloroauric acid is reduced with sodium citrate.

As the method for sensitizing the detection reagent to the colloidal metal particles, a known method such as physical adsorption or chemical binding can be used. For example, the detection reagent in which an antibody is sensitized to the colloidal gold particles is prepared by adding an antibody to a solution in which gold particles are colloidally dispersed to cause a physical adsorption, and thereafter adding a bovine serum albumin solution thereto to block the surface of the particle to which the antibody is not bound.

In the implementation of actual immunochromatographic analysis, the detection reagent labeled with the insoluble carrier can be applied by dispersing the detection reagent in a developing solution constituting the mobile phase, or can also be applied by allowing the detection reagent to exist on a pathway on which the mobile phase is developed and migrates in the chromatography medium constituting the stationary phase, that is, in a region between an end part to which the mobile phase in the chromatography medium is applied and the reaction region.

In the case where the detection reagent is allowed to exist on the chromatography medium, it is preferred to support the detection reagent so that the detection reagent is promptly dissolved in the developing solution and can freely migrate by a capillary action. In a region where the detection reagent is supported, in order to enhance the resolubility of the insoluble carrier to which the detection reagent is sensitized, a saccharide such as saccharose, maltose, or lactose, or a sugar alcohol such as mannitol can be added and applied thereto or the region can also be coated with such a substance in advance.

When the detection reagent is allowed to exist on the chromatography medium by applying, drying, and the like, the detection reagent can be directly applied to the chromatography medium having the immobilizing reagent immobilized thereon, followed by drying and the like, or the detection reagent may be applied to another porous material, for example, a cellulose filter paper, a glass fiber filter paper, or a nylon non-woven fabric, followed by drying and the like, thereby forming a detection reagent retaining member, and thereafter, the detection reagent retaining member may be disposed so as to be connected to the chromatography medium having the immobilizing reagent immobilized thereon through a capillary.

The detection target to be detected by the method of the present invention is not particularly limited as long as there exists a substance which specifically binds thereto, and examples thereof include proteins, peptides, nucleic acids, sugars (particularly, a sugar moiety of a glycoprotein, a sugar moiety of a glycolipid, etc.), and glycoconjugates.

In the present invention, the phrase "specifically binding" refers to binding based on the affinity of a biomolecule. Examples of such binding based on the affinity include binding between an antigen and an antibody, binding between a sugar and a lectin, binding between a hormone and a receptor, binding between an enzyme and an inhibitor, binding between complementary nucleic acids, and binding between a nucleic acid and a nucleic acid-binding protein.

Therefore, in the case where the detection target has antigenicity, examples of the substance which specifically binds to the detection target include a polyclonal antibody and a monoclonal antibody. Further, in the case where the detection target is a sugar, examples of the substance which specifically binds to the detection target include lectin proteins.

Specific examples of the detection target include carcinoembryonic antigen (CEA), HER2 protein, prostate specific antigen (PSA), CA19-9, α-fetoprotein (AFP), immunosuppressive acidic protein (IPA), CA15-3, CAl25, estrogen receptor, progesterone receptor, fecal occult blood, troponin I, troponin T, CK-MB, CRP, human chorionic gonadotropin (hCG), luteinizing hormone (LH), follicle-stimulating hormone (FSH), syphilis antibody, influenza virus, human hemoglobin, *chlamydia* antigen, group A β-hemolytic streptococcal antigen, HBs antibody, HBs antigen, rotavirus, adenovirus, albumin, and glycated albumin, however, the detection target is not limited thereto.

(3) Step of Developing Analyte and Labeling Substance in Chromatography Medium Part as Mobile Phase in the Presence of Nonionic Surfactant The step (3) is a step in which after the detection target is recognized by the labeling substance in the step (2), the analyte and the labeling substance are allowed to pass on the chromatography medium part (3) as a mobile phase in the presence of a nonionic surfactant.

The nonionic surfactant is made to exist in advance in the process of developing the analyte and the labeling substance in the chromatography medium part as a mobile phase. It is preferred that the nonionic surfactant is contained in the sample addition part in advance as described above or the nonionic surfactant is contained in the analyte dilution solution.

This is because by containing the nonionic surfactant in advance, the decrease in the detection sensitivity due to adsorption of the analyte on the member of the sample dropping part can be prevented, and by decreasing the surface tension of the sample solution, the determination time can be shortened. It is more preferred that the nonionic surfactant is contained in the analyte dilution solution.

By containing the nonionic surfactant in the analyte dilution solution, the component in the sample can be made uniform in advance, and an effect of suppressing the adsorption on the member can be expected more than in the case of containing the nonionic surfactant in the member. In addition, this is because there is no elution time of the nonionic surfactant in the sample dropping part, and therefore, the determination time can be further shortened. The nonionic surfactant may be contained in both of the sample addition part and the analyte dilution solution.

In the immunochromatographic analysis method of the present invention, a developing solution may be used as needed. The developing solution is a liquid constituting the mobile phase in the immunochromatography method, and migrates along with the sample containing the detection target and the labeled detection reagent on the chromatography medium serving as the stationary phase. The developing solution may be any as long as it is a developing solution as described above.

(4) Step of Detecting Detection Target in Developed Mobile Phase in Detection Part The step (4) is a step in which the detection target in the analyte passing on the chromatography medium part (3) as the mobile phase is specifically reacted and bound so as to be sandwiched like a sandwich by the antibody and the labeling reagent retained in the detection part (4), that is, supported and fixed thereto, by an antigen-antibody specific binding reaction, and the detection part (4) is colored.

In the case where the detection target is not present, the labeling reagent dissolved in an aqueous component of the sample does not cause a specific binding reaction even if it passes through the detection part (4) on the chromatography medium part (3), and therefore, the detection part (4) is not colored.

Finally, the aqueous component of the analyte-containing solution migrates to the absorption part (5).

In this manner, by testing the presence or absence of the detection target contained in the analyte, for example, an influenza virus in the analyte-containing solution, the presence or absence of infection with the influenza virus can be accurately determined.

EXAMPLES

Hereinafter, the present invention will be further described by way of Examples and Comparative Examples, however, the present invention is not limited to the following Examples.

Examples 1 to 4

(1) Preparation of Detection Part on Chromatography Medium

As a membrane, a sheet composed of nitrocellulose (manufactured by Millipore, Inc., trade name: HF 120, 300 mm×25 mm) was used. As a pretreatment, the membrane was immersed in a 0.25 mass % aqueous solution of an anionic surfactant shown in Table 1, followed by drying at 30° C. for 24 hours.

Subsequently, 150 μL of a solution obtained by diluting a mouse-derived anti-influenza A monoclonal antibody (first antibody) with a phosphate buffer solution (pH 7.4) containing 5 mass % isopropyl alcohol to a concentration of 1.0 mg/mL was applied to a detection region (detection line) with a width of 1 mm on the membrane in which the anionic surfactant was contained and dried, and in order to confirm the presence or absence of development of a gold nanoparticle labeling reagent or the developing speed, on the downstream of the detection region, a solution obtained by diluting a goat-derived antiserum having affinity in a wide range for the gold nanoparticle labeling substance, animal meat proteins to be used as the detection target, and the like with a phosphate buffer solution (pH 7.4) was applied to a control region (control line). Thereafter, the solution was dried at 50° C. for 30 minutes, and then dried at room temperature overnight, whereby a chromatography medium was prepared.

(2) Preparation of Labeling Substance Solution

To 0.5 mL of a colloidal gold suspension (manufactured by Tanaka Kikinzoku Kogyo K.K., LC 40 nm), 0.1 mL of a mouse-derived anti-influenza A monoclonal antibody (second antibody) diluted with a phosphate buffer solution (pH 7.4) to a concentration of 0.05 mg/mL was added, and the resulting mixture was left to stand at room temperature for 10 minutes.

Subsequently, 0.1 mL of a phosphate buffer solution (pH 7.4) containing 1 mass % bovine serum albumin (BSA) was added thereto, and the resulting mixture was left to stand at room temperature for an additional 10 minutes. Thereafter, the mixture was thoroughly stirred, and then centrifuged at 8000×g for 15 minutes. After removing the supernatant, 0.1 mL of a phosphate buffer solution (pH 7.4) containing 1 mass % BSA was added thereto. According to the above-mentioned procedure, a labeling substance solution was prepared.

(3) Preparation of Sample Addition Part

As a sample addition part, a non-woven fabric composed of glass fiber (manufactured by Millipore, Inc., 30 mm×30 mm) was immersed in a 2 mass % aqueous solution of a nonionic surfactant shown in Table 1, followed by drying at 30° C. for 24 hours, whereby a sample addition part was prepared. The type of the nonionic surfactant contained in the prepared sample addition part and the HLB value and content thereof are shown in Table 1. In Table 1, TWEEN 20 is polyoxyethylene (20) sorbitan monolaurate, Tween 80 is polyoxyethylene (20) sorbitan monooleate, and TRITON X-100 is polyoxyethylene (10) octylphenyl ether, and all are manufactured by Wako Pure Chemical Industries, Ltd. Further, NP-40 is (octylphenoxy)polyethoxyethanol, and manufactured by Sigma-Aldrich Corporation.

(4) Preparation of Immunochromatographic Analysis Device

A solution obtained by adding 300 μL of a 10 mass % aqueous solution of trehalose and 1.8 mL of distilled water to 300 μL of the above-prepared labeling substance solution was added uniformly to a 15 mm×300 mm glass fiber pad (manufactured by Millipore, Inc.), followed by drying in a vacuum dryer, whereby a labeling substance retaining member was prepared.

Subsequently, to a base material composed of a backing sheet, the above-prepared chromatography medium, labeling substance retaining member, and sample addition part to be used in a portion to which a sample is added, and a non-woven fabric (density: 0.25 g/cm$^3$) made of glass fiber as an absorption part for absorbing the developed sample and labeling substance were bonded. Then, the resulting material was cut to a width of 5 mm by a cutting machine, whereby an immunochromatographic analysis device was prepared. The type of the non-woven fabric used for the absorption part and the filtering time of the absorption part are shown in Table 1.

The filtering time was measured in accordance with JIS P 3801:1995.

(5) Analyte Dilution Solution

A 50 mM BICINE buffer solution (pH 8.5) containing 2 mass % casein, 25 mM KCl, and 0.095% sodium azide was prepared and used as an analyte dilution solution.

(6) Measurement

By using the above-prepared test piece for immunochromatography, the presence or absence of influenza A virus in the sample was measured according to the following method. That is, one tube of a suction trap was inserted into a suction pump, and the other tube was inserted deep into the nasal cavity of a person who was not infected with influenza, and a nasal discharge was collected by setting the suction pump to a negative pressure. The thus collected nasal discharge was diluted 20 times with the above analyte dilution solution, and the diluted solution was used as a negative analyte sample. Further, a positive analyte sample was prepared by adding a commercially available inactivated influenza A virus to the negative analyte sample so that the protein concentration was 50 ng/mL.

The negative analyte sample and the positive analyte sample in an amount of 150 µL each were placed on the sample addition part of the test piece for immunochromatography and developed, and after 10 minutes, visual determination was performed. A case where a red line of the test line could be confirmed was evaluated as "+", a case where a red line could be confirmed, but the color of the line was very light was evaluated as "±", and a case where a red line could not be confirmed was evaluated as "−".

In addition, the presence or absence of coloration of the background at 10 minutes after the start of the test, and the presence or absence of backward flow of the developed component and a false-positive result (only the negative analyte) at 60 minutes after the start of the test were observed. The test results are shown in Table 1.

The coloration of the background is derived from the labeling substance (gold nanoparticles) to be developed, and when the red gold nanoparticles are completely absorbed in the absorption pad, the background is decolored and the original white color of the chromatography medium comes to be observed. In Table 1, a case where the color of the background was the original white color of the chromatography medium or a color equivalent thereto is shown as "A" (good), a case where the color of the background was slightly reddish is shown as "B" (slightly bad), and a case where the color of the background was reddish is shown as "C" (bad).

The color tone of the chromatography medium looks different between in a dry state and in a wet state, and therefore, the backward flow of the developed component was determined by visually observing the color tone of the chromatography medium. The evaluation of the backward flow of the developed component was performed such that a case where the coloration of the background after 60 minutes was became worse (the color became more reddish) than after 10 minutes was evaluated as "presence", and the other cases were evaluated as "absence".

The presence or absence of a false-positive result was determined by observing whether or not a red line derived from the labeling substance (gold nanoparticles) is generated in the detection part of the chromatography medium at 60 minutes after the start of the test. The sample used was a sample determined as negative in a test by a PCR method, and also in a test using a test kit by immunochromatography, a red line which shows a positive result was not observed in the detection part at 15 minutes after the start of the test. However, in the case where backward flow of the developed component occurs, at 60 minutes after the start of the test, a red line is sometimes generated in the detection part, and this case was determined that a false-positive result is present. The results are shown in Table 1.

Example 5

(1) Preparation of Detection Part on Chromatography Medium

A detection part was prepared in the same manner as in Examples 1 to 4.

(2) Preparation of Labeling Substance Solution

A labeling substance solution was prepared in the same manner as in Examples 1 to 4.

(3) Preparation of Sample Addition Part

A sample addition part was prepared in the same manner as in Examples 1 to 4.

(4) Preparation of Immunochromatographic Analysis Device

An immunochromatographic analysis device was prepared in the same manner as in Examples 1 to 4.

(5) Analyte Dilution Solution

A 50 mM BICINE buffer solution (pH 8.5) containing 2 mass % casein, 25 mM KCl, and 0.095% sodium azide was prepared, and 2 mass % Tween 80 was mixed therein so that the content thereof was as shown, whereby an analyte dilution solution was prepared.

(6) Measurement

The measurement was performed in the same manner as in Examples 1 to 4, and evaluation was performed. The results are shown in Table 1.

Examples 6 to 8

(1) Preparation of Detection Part on Chromatography Medium

A detection part was prepared in the same manner as in Examples 1 to 5.

(2) Preparation of Labeling Substance Solution

A labeling substance solution was prepared in the same manner as in Examples 1 to 5.

(3) Preparation of Sample Addition Part

As a sample addition part, a non-woven fabric composed of glass fiber (manufactured by Millipore, Inc., 30 mm×30 mm) was used.

(4) Preparation of Immunochromatographic Analysis Device

An immunochromatographic analysis device was prepared in the same manner as in Examples 1 to 5.

(5) Analyte Dilution Solution

A 50 mM BICINE buffer solution (pH 8.5) containing 2 mass % casein, 25 mM KCl, and 0.095% sodium azide was prepared, and a nonionic surfactant shown in Table 1 was mixed therein so that the content thereof was as shown, whereby an analyte dilution solution was prepared. In Table 1, IGAPEL CA-520 is polyoxyethylene (5) isooctylphenyl ether and is manufactured by Sigma-Aldrich Corporation.

(6) Measurement

The measurement was performed in the same manner as in Examples 1 to 5, and evaluation was performed. The results are shown in Table 1.

Comparative Examples 1 and 2

(1) Preparation of Detection Part on Chromatography Medium

A detection part was prepared in the same manner as in Examples.

(2) Preparation of Labeling Substance Solution

A labeling substance solution was prepared in the same manner as in Examples.

(3) Preparation of Sample Addition Part

As a sample addition part, a non-woven fabric composed of glass fiber (manufactured by Millipore, Inc., 30 mm×30 mm) was used.

(4) Preparation of Immunochromatographic Analysis Device

A solution obtained by adding 300 μL of a 10 mass % aqueous solution of trehalose and 1.8 mL of distilled water to 300 μL of the above-prepared labeling substance solution was added uniformly to a 15 mm×300 mm glass fiber pad (manufactured by Millipore, Inc.), followed by drying in a vacuum dryer, whereby a labeling substance retaining member was prepared.

Subsequently, to a base material composed of a backing sheet, the above-prepared chromatography medium, labeling substance retaining member, and sample addition part to be used in a portion to which a sample is added, and a non-woven fabric as an absorption part for absorbing the developed sample and labeling substance were bonded. Then, the resulting material was cut to a width of 5 mm by a cutting machine, whereby an immunochromatographic analysis device was prepared. The type of the non-woven fabric used for the absorption part and the filtering time of the absorption part are shown in Table 1.

The filtering time was measured in accordance with JIS P 3801:1995.

(5) Analyte Dilution Solution

A 50 mM BICINE buffer solution (pH 8.5) containing 2 mass % casein, 25 mM KCl, and 0.095% sodium azide was prepared, and a nonionic surfactant shown in Table 1 was mixed therein so that the content thereof was as shown, whereby an analyte dilution solution was prepared.

(6) Measurement

The measurement was performed in the same manner as in Examples, and evaluation was performed. The results are shown in Table 1.

Comparative Example 3

(1) Preparation of Detection Part on Chromatography Medium

A detection part was prepared in the same manner as in Examples.

(2) Preparation of Labeling Substance Solution

A labeling substance solution was prepared in the same manner as in Examples.

(3) Preparation of Sample Addition Part

As a sample addition part, a non-woven fabric composed of glass fiber (manufactured by Millipore, Inc., 30 mm×30 mm) was used.

(4) Preparation of Immunochromatographic Analysis Device

An immunochromatographic analysis device was prepared in the same manner as in Examples.

(5) Analyte Dilution Solution

A 50 mM BICINE buffer solution (pH 8.5) containing 2 mass % casein, 25 mM KCl, and 0.095% sodium azide was prepared, whereby an analyte dilution solution was prepared.

(6) Measurement

The measurement was performed in the same manner as in Examples, and evaluation was performed. The results are shown in Table 1.

TABLE 1

| | | Sample addition part | | | Analyte dilution solution | | | Absorption part | | | |
|---|---|---|---|---|---|---|---|---|---|---|---|
| | Membrane Surfactant | Nonionic surfactant | HLB value | Content (μg/cm$^2$) | Nonionic surfactant | HLB value | Content (mass %) | Non-woven fabric | Filtering time (sec) | Density (g/cm$^3$) | Test subject |
| Example 1 | Na dodecylbenzene sulfate | Tween 20 | 16.7 | 2.0 | — | — | — | Glass fiber | 58 | 0.25 | negative positive |
| Example 2 | Na dodecylbenzene sulfate | Tween 80 | 15 | 1.0 | — | — | — | Glass fiber | 20 | 0.33 | negative positive |
| Example 3 | Na dodecylbenzene sulfate | Triton X-100 | 13.5 | 4.0 | — | — | — | Glass fiber | 58 | 0.25 | negative positive |
| Example 4 | Na dodecyl sulfate | NP-40 (nonylphenyl ethoxylate) | 17.8 | 2.0 | — | — | — | Glass fiber | 84 | 0.21 | negative positive |
| Example 5 | Na C12-18 alkyl sulfate | Tween 20 | 16.7 | 0.2 | Tween 80 | 15 | 0.05 | Glass fiber | 58 | 0.25 | negative positive |
| Example 6 | Na dodecylbenzene sulfate | — | — | — | Tween 80 | 15 | 2.0 | Glass fiber | 58 | 0.25 | negative positive |
| Example 7 | Na dodecylbenzene sulfate | — | — | — | NP-40 | 17.8 | 1.0 | Glass fiber | 58 | 0.25 | negative positive |
| Example 8 | Na dodecylbenzene sulfate | — | — | — | IGAPEL CA-520 | 9.1 | 3.5 | Glass fiber | 58 | 0.25 | negative positive |
| Comparative Example 1 | Na dodecylbenzene sulfate | — | — | — | Tween 20 | 16.7 | 1.0 | Cotton linter | 55 | 0.54 | negative positive |
| Comparative Example 2 | Na dodecylbenzene sulfate | — | — | — | Tween 20 | 16.7 | 1.0 | Cellulose fiber | 60 | 0.44 | negative positive |
| Comparative Example 3 | Na dodecylbenzene sulfate | — | — | — | — | — | — | Glass fiber | 58 | 0.25 | negative positive |

TABLE 1-continued

| | | Results | | | | |
|---|---|---|---|---|---|---|
| | Determination | Coloration of background after 10 minutes | Coloration of background after 60 minutes | Presence or absence of backward flow | Presence or absence of false-positive result | Development speed |
| Example 1 | − | A | A | absence | absence | 90 |
| | + | A | A | absence | — | 93 |
| Example 2 | − | A | A | absence | absence | 95 |
| | + | A | A | absence | — | 93 |
| Example 3 | − | A | A | absence | absence | 114 |
| | + | A | A | absence | — | 120 |
| Example 4 | − | A | A | absence | absence | 130 |
| | + | A | A | absence | — | 129 |
| Example 5 | − | A | A | absence | absence | 130 |
| | + | A | A | absence | — | 125 |
| Example 6 | − | A | A | absence | absence | 118 |
| | + | A | A | absence | — | 117 |
| Example 7 | − | A | A | absence | absence | 120 |
| | + | A | A | absence | — | 117 |
| Example 8 | − | A | A | absence | absence | 133 |
| | + | A | A | absence | — | 145 |
| Comparative Example 1 | ± | A | C | presence | presence | 110 |
| | + | A | C | presence | — | 112 |
| Comparative Example 2 | ± | A | B | presence | presence | 120 |
| | + | A | B | presence | — | 110 |
| Comparative Example 3 | ± | B | B | absence | presence | 182 |
| | + | B | B | absence | — | 158 |

As shown in Table 1, in Examples 1 to 8, when glass fiber was used for the absorption part, and the analyte and the labeling substance were developed in the chromatography medium part as the mobile phase in the presence of the nonionic surfactant, the return of the liquid of the sample was not confirmed, and as a result, a false-positive result was not observed.

On the other hand, in Comparative Example 1, cotton linter was used for the absorption part, and in Comparative Example 2, cellulose fiber was used for the absorption part, and as a result, the return of the liquid of the sample was confirmed, and a false-positive result was observed.

Further, in Comparative Example 3, glass fiber was used for the absorption part, however, as a result of developing the analyte and the labeling substance in the chromatography medium part as the mobile phase in the absence of a nonionic surfactant, although the return of the liquid of the sample was not confirmed, a false-positive reaction was observed.

It is considered that since a nonionic surfactant was not present, the developing speed was decreased, and also the peel speed of the developed component was decreased, and therefore, although the backward flow of the developed component did not occur, the labeling reagent was retained on the chromatography medium, and therefore, no change was observed in the coloration of the background between after 10 minutes and after 60 minutes, and thus, a false-positive result was observed.

From the above results, it was found that when the analyte and the labeling substance are developed in the chromatography medium part as the mobile phase in the presence of a nonionic surfactant, the developing speed of the sample can be increased, and also even when the developing speed of the sample is increased, by using the glass fiber for the absorption part, the return of the liquid of the developed component can be reduced, and thus, a false-positive result can be avoided.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2014-077861) filed on Apr. 4, 2014 and the entire contents of which are incorporated herein by reference.

REFERENCE SIGNS LIST 1. sample addition part (sample pad)
2. labeling substance retaining part (conjugate pad)
3. chromatography medium part
4. detection part
5. absorption part
6. backing sheet

The invention claimed is:

1. An immunochromatographic analysis method, which is a method for detecting a detection target contained in an analyte using an immunochromatographic analysis device which includes a sample addition part, a labeling substance retaining part, a chromatography medium part having a detection part supported thereon, and an absorption part that has a filtering time from 20 to 110 seconds and a density of 200 to 350 mg/cm$^3$ and is composed of glass fiber, comprising the following steps (1) to (4):

(1) a step of adding an analyte-containing solution obtained by diluting the analyte with an analyte dilution solution to the sample addition part;
   (2) a step of allowing a labeling substance retained in the labeling substance retaining part to recognize the detection target;
   (3) a step of allowing the analyte and the labeling substance in the chromatography medium part as a mobile phase in the presence of a nonionic surfactant to be developed; and
   (4) a step of detecting the detection target in the developed mobile phase in the detection part.

2. The method according to claim 1, wherein the nonionic surfactant is contained in at least one of the sample addition part and the analyte dilution solution.

3. The method according to claim 2, wherein the content of the nonionic surfactant in the sample addition part is from 0.05 to 5 mg per cm$^2$.

4. The method according to claim 2, wherein the content of the nonionic surfactant in the analyte dilution solution is from 0.05 to 10 mass %.

5. The method according to claim 1, wherein the hydrophilic-lipophilic balance value of the nonionic surfactant is 10 or more.

6. The method according to claim 1, wherein the chromatography medium part contains an anionic surfactant.

7. The method according to claim 6, wherein the content of the anionic surfactant in the chromatography medium part is from 0.02 to 4 mass %.

8. The method according to claim 1, wherein the chromatography medium part is composed of nitrocellulose.

9. An immunochromatographic analysis device, sequentially comprising a sample addition part, a labeling substance retaining part, a chromatography medium part having a detection part supported thereon, and an absorption part, wherein the sample addition part retains a nonionic surfactant in a dry state, and the absorption part has a filtering time from 20 to 110 seconds and a density of 200 to 350 mg/cm$^3$ and is composed of glass fiber.

10. An immunochromatographic analysis kit, comprising an immunochromatography device, which sequentially includes a sample addition part, a labeling substance retaining part, a chromatography medium part having a detection part supported thereon and an absorption part, and an analyte dilution solution for diluting a detection target contained in an analyte, wherein the absorption part has a filtering time from 20 to 110 seconds and a density of 200 to 350 mg/cm$^3$ and is composed of glass fiber, and the analyte dilution solution contains a nonionic surfactant.

11. The method according to claim 2, wherein the hydrophilic-lipophilic balance value of the nonionic surfactant is 10 or more.

12. The method according to claim 3, wherein the hydrophilic-lipophilic balance value of the nonionic surfactant is 10 or more.

13. The method according to claim 4, wherein the hydrophilic-lipophilic balance value of the nonionic surfactant is 10 or more.

14. The method according to claim 2, wherein the chromatography medium part contains an anionic surfactant.

15. The method according to claim 3, wherein the chromatography medium part contains an anionic surfactant.

16. The method according to claim 4, wherein the chromatography medium part contains an anionic surfactant.

17. The method according to claim 5, wherein the chromatography medium part contains an anionic surfactant.

18. The method according to claim 2, wherein the chromatography medium part is composed of nitrocellulose.

* * * * *